(12) United States Patent
Eckelman et al.

(10) Patent No.: US 10,526,397 B2
(45) Date of Patent: Jan. 7, 2020

(54) NON-IMMUNOGENIC SINGLE DOMAIN ANTIBODIES

(71) Applicant: Inhibrx, Inc., La Jolla, CA (US)

(72) Inventors: Brendan P. Eckelman, La Jolla, CA (US); John C. Timmer, La Jolla, CA (US); Quinn Deveraux, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 17 days.

(21) Appl. No.: 15/003,234

(22) Filed: Jan. 21, 2016

(65) Prior Publication Data

US 2016/0207981 A1 Jul. 21, 2016

Related U.S. Application Data

(60) Provisional application No. 62/106,035, filed on Jan. 21, 2015.

(51) Int. Cl.
*C07K 16/00* (2006.01)
*C07K 16/42* (2006.01)

(52) U.S. Cl.
CPC .......... *C07K 16/00* (2013.01); *C07K 16/4283* (2013.01); *C07K 2317/24* (2013.01); *C07K 2317/56* (2013.01); *C07K 2317/567* (2013.01); *C07K 2317/569* (2013.01)

(58) Field of Classification Search
CPC .............. C07K 16/00; C07K 2317/24; C07K 2317/567; C07K 2317/569
USPC ..................................... 530/387.3; 424/133.1
See application file for complete search history.

(56) References Cited

U.S. PATENT DOCUMENTS

| 8,575,070 B2 | 11/2013 | Watt et al. |
| 2014/0161796 A1 | 6/2014 | Loew et al. |

FOREIGN PATENT DOCUMENTS

| WO | 2006091734 A2 | 8/2006 |
| WO | 2007066106 A1 | 6/2007 |
| WO | 2010115141 A2 | 7/2010 |
| WO | 2010115141 A2 | 10/2010 |
| WO | 2013024059 A9 | 4/2014 |
| WO | 2014111550 A1 | 7/2014 |

OTHER PUBLICATIONS

Cordy, J.C., et al. "Specificity of Human Anti-Variable Heavy (Vh) Chain Autoantibodies and Impact on the Design and Clinical Testing of a Vh Domain Antibody Antagonist of Tumour Necrosis Factor-a Receptor 1," British Society for Immunology, Clinical and Experimental Immunology, 182, (2015) pp. 139-148.
Holland, M.C. et al., "Autoantibodies to Variable Heavy (VH) Chain Ig Sequences in Humans Impact the Safety and Clinical Pharmacology of a Vh Domain Antibody Antagonist of TNF-a Receptor 1," J. Clin Immunol (2013) 33:1192-1203.
International Search Report for PCT/US2016/014296 dated Jul. 1, 2016, 6 pages.
Papadopoulos, K. et al., "Unexpected Hepatotoxicity in a phase I study of TAS266, a Novel Tetravalent Agonistic Nanobody Targeting the DR5 Receptor," Cancer Chemother Pharmacol (2015) pp. 887-895.
International Preliminary Report on Patentability issued in PCT/US2016/014296, dated Jun. 6, 2016, 6 pages.
UniProt Accession M0J6E7 _9EURY (Oct. 1, 2014) [Retrieved from the Internet May 30, 2016: <http://www.uniprot.org/uniprot/M0J6E7.txt?version=4>J; amino acids 143-150, 100% identity); 1 page.
Vaneycken et al., "In Vitro Analysis and In Vivo Tumor Targeting of Humanized, Grafted Nanobody in Mice Using Pinhole SPECT/Micro-CT," The Journal of Nuclear Medicine, vol. 51, No. 7, Jul. 2010, 9 pages.
Yin et al., "Characterization of Asia 1 sdAb from Camels Bactrianus (C. bactrianus) and Conjugation with Quantum Dots for Imaging FMDV in BHK-21 Cells," PLOS One, vol. 8, Issue 5, May 2013, 10 pages.
European Search Report issued in 16740748.5, dated Jul. 25, 2018, 7 pages.
Harmsen et al. "Selection and optimization of proteolytically stable llama single-domain antibody fragments for oral immunotherapy." Applied Microbiology and Biotechnology, 72(3): 544-551 (2006).
Hussack et al. "Engineered Single-Domain Antibodies with Hight Protrase Resistance and Thermal Stability." PLOS One, 6(11): e28218, 15 pages (2011).
Muyldermans "Nanobodies Natural Single-Domain Antibodies." Annual REview of Biochemistry 82(1): 775-797 (2013).

*Primary Examiner* — Lynn A Bristol
(74) *Attorney, Agent, or Firm* — McNeill Baur PLLC

(57) ABSTRACT

The invention provides modifications within human or humanized single domain antibody fragments (sdAbs) that prevent recognition by pre-existing antibodies, to isolated polypeptides that include these modifications, and to methods and uses thereof.

24 Claims, 5 Drawing Sheets

Specification includes a Sequence Listing.

Figure 4

NON-IMMUNOGENIC SINGLE DOMAIN ANTIBODIES

RELATED APPLICATIONS

This application claims the benefit of U.S. Provisional Application No. 62/106,035, filed Jan. 21, 2015, the contents of which are incorporated herein by reference in their entirety.

FIELD OF THE INVENTION

This invention relates generally to modifications within human or humanized single domain antibody fragments (sdAbs) that prevent recognition by pre-existing antibodies, to isolated polypeptides that include these modifications, and to methods and uses thereof.

INCORPORATION OF SEQUENCE LISTING

The contents of the text file named "INHI018001WO_ST25", which was created on Jan. 20, 2016 and is 10.0 KB in size, are hereby incorporated by reference in their entirety.

BACKGROUND OF THE INVENTION

Clinical immunogenicity of biotherapeutics can limit efficacy and contribute to adverse events. Both cellular and humoral immunogenicity can be problematic in a clinical setting. Most often observed in antibodies derived from non-human sources, immunogenicity or the threat thereof has led to extensive protein engineering and platform innovations to mitigate potential immunogenicity. These include humanization, humaneering, veneering, and development of fully human antibody platforms. However, even fully human antibodies and antibody fragments have the risk of being immunogenic. Immunogenicity is often directed toward the CDR regions of an antibody. Conversely, framework region-directed immunogenicity has also been observed, as in the case of single domain antibodies. It has been noted that a significant proportion of people have pre-existing antibodies to the cryptic epitopes within single domain antibodies. Therefore, there exists a need for the generation non-immunogenic single domain antibodies.

SUMMARY OF THE INVENTION

The modified single domain antibody (sdAb) fragments, of the present invention can be derived from numerous sources, including but not limited to $V_H H$, $V_{NAR}$, engineered $V_H$ or $V_K$ domains. $V_H Hs$ can be generated from camelid heavy chain only antibodies and libraries thereof. $V_{NAR}s$ can be generated from cartilaginous fish heavy chain only antibodies and libraries thereof. Various methods have been implemented to generate monomeric sdAbs from conventionally heterodimeric $V_H$ and $V_K$ domains, including interface engineering and selection of specific germline families. In preferred embodiments the modified sdAb of the present invention are human or humanized.

Pre-existing anti-human single domain antibody (sdAb) antibodies (ASDA) are most prevalently observed in formats wherein an sdAb is positioned such that is has a free carboxy-terminus. The present invention provides mutations within the human or humanized sdAb regions that disable ASDA recognition. In some embodiments of the present invention, the sdAb is altered or modified within the framework 1 region (FW1). In other embodiments, the sdAb is altered or modified within the framework 2 region (FW2). In other embodiments, the sdAb is altered or modified within the framework 3 region (FW3). In other embodiments, the sdAb is altered or modified within the framework 4 region (FW4). These modifications include mutations, truncation, extensions, or a combination thereof. In some embodiments, the sdAb is modified within a single region. In other embodiments, the sdAb is modified at more than one region. For example, an sdAb may be modified within framework 1 and framework 4. The sdAb modifications of the present invention disable ASDA recognition without substantially decreasing binding affinity, specificity, expressability or stability of the protein. All numbering used herein refers to Kabat Numbering.

Exemplary modifications with the framework 4 of the sdAb are shown below aligned to the human VH carboxy-terminal residues (Leu/Thr108, Val109, Thr110, Val111, Ser112, Ser113; LVTVSS):

```
108 LVTVSS 113
(natural human VH sequence, SEQ ID NO: 58)

(SEQ ID NO: 1)
108 LVEIK 112

(SEQ ID NO: 2)
108 LVTVE 112

(SEQ ID NO: 3)
108 LVTVSE 113

(SEQ ID NO: 4)
108 LVTVEG 113

(SEQ ID NO: 5)
108 LVTVSEG 114

(SEQ ID NO: 6)
108 LVTVK 112

(SEQ ID NO: 7)
108 LVTVS 112

(SEQ ID NO: 8)
108 LVTVSK 113

(SEG ID NO: 9)
108 LVTVKG 113

(SEQ ID NO: 10)
108 LVTVSKG 114

(SEQ ID: NO 30)
108 LVTVSKPG 115

(SEQ ID: NO 31)
108 LVTVSKPGG 116

(SEQ ID: NO 32)
108 LVTVKP 113

(SEQ ID: NO 33)
108 LVTVKPG 114

(SEQ ID: NO 34)
108 LVTVKPGG 115

(SEQ ID: NO 35)
108 LVTVRP 113

(SEQ ID: NO 36)
108 LVTVRPG 114

(SEQ ID: NO 37)
108 LVTVRPGG 115
```

```
                                (SEQ ID: NO 38)
108 LVTVEP 113

(SEQ ID: NO 39)
108 LVTVEPG 114

(SEQ ID: NO 40)
108 LVTVEPGG 115

(SEQ ID: NO 41)
108 LVTVDP 113

(SEQ ID: NO 42)
108 LVTVDPG 114

(SEQ ID: NO 43)
108 LVTVDPGG 115

(SEQ ID NO: 11)
108 EVTVSS 113

(SEQ ID NO: 12)
108 KVTVSS 113

(SEQ ID NO: 13)
108 LVEVSS 113

(SEQ ID NO: 14)
108 LVKVSS 113

(SEQ ID NO: 15)
108 EVEVSS 113

(SEQ ID NO: 16)
108 EVKVSS 113

(SEQ ID NO: 17)
108 KVKVSS 113

(SEQ ID NO: 18)
108 KVEVSS 113
```

Exemplary carboxy-terminal extensions to the sdAb are shown below aligned to the human VH carboxy-terminal residues (Leu/Thr108, Val109, Thr110, Val111, Ser112, Ser113; LVTVSS):

```
108 LVTVSS 113
(natural human VH sequence, SEQ ID NO: 58)

(SEQ ID NO: 19)
108 LVTVSSA 114

(SEQ ID NO: 20)
108 LVTVSSG 114

(SEQ ID NO: 21)
108 LVTVSSGG 115

(SEQ ID NO: 22)
108 LVTVSSGGG 116

(SEQ ID NO: 23)
108 LVTVSSGGGG 117
```

In some embodiments the sdAb is modified at position Leu11 within framework 1. For example, the modification at position Leu11 is Leu11Lys (L11K), Leu11Arg (L11R), Leu11Glu (L11E) or Leu11Asp (L11D). In some embodiments, the sdAb is modified position Leu11 and within its carboxy-terminal region. For example L11K, L11R, L11E or L11D and comprising the terminal sequence of TVE, TVSE (SEQ ID NO: 24), TVEG (SEQ ID NO: 25), TVSEG (SEQ ID NO: 26), TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), TVRPGG (SEQ ID NO: 51), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), TVDPGG (SEQ ID NO: 57).

In some embodiments, the sdAb is modified at position 11 with a positively charged residue (e.g. L11K or L11R) and paired with a carboxy-terminal modification that contains a negatively charged residue at position 112 or 113. For example, L11K or L11R is paired with carboxy-terminal modification of TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), or TVDPGG (SEQ ID NO: 57).

In some embodiments, the sdAb is modified at position 11 with a negatively charged residue (e.g. L11E or L11D) and is paired with a carboxy-terminal modification that contains a positively charged residue at position 112 or 113. For example, L11E or L11D is paired with carboxy-terminal modification of TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), or TVRPGG (SEQ ID NO: 51).

In some embodiments, the sdAb is modified at position 11 with a positively charged residue (e.g. L11K or L11R) and paired with a carboxy-terminal modification that contains a positively charged residue at position 112 or 113. For example, L11K or L11R is paired with carboxy-terminal modification of TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), or TVRPGG (SEQ ID NO: 51).

In some embodiments, the sdAb is modified at position 11 with a negatively charged residue (e.g. L11E or L11D) and paired with a carboxy-terminal modification that contains a negatively charged residue at position 112 or 113. For example, L11E or L11D is paired with carboxy-terminal modification of TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), or TVDPGG (SEQ ID NO: 57).

Presumably, in embodiments wherein there are opposing charged residues introduced into position 11 and 112 or position 11 and 113 of the sdAb, a new electrostatic interaction enabled by the newly added negative and positive charge pair. Presumably, in embodiments, wherein the residues introduced at position 11 and 112 or position 11 and 113, are of the same charge, the orientation of these sides of these amino acids will be position away from each other, however, are still capable of occluding the recognition site be pre-existing ASDA recognition of the modified sdAb.

In some embodiments, the sdAb is modified at position Ala88 within framework 3. For example, the modification at position Ala88 is Ala88Glu (A88E), Ala88Asp (A88D), Ala88Lys (A88K) or Ala88Arg (A88R). In some embodiments, the sdAb is modified position Ala88 and within its carboxy-terminal region. For example A88E, A88D, A88K or A88R and comprising the terminal sequence of TVE, TVSE (SEQ ID NO: 24), TVEG (SEQ ID NO: 25), TVSEG (SEQ ID NO: 26), TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), TVRPGG (SEQ ID NO: 51), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), or TVDPGG (SEQ ID NO: 57).

In some embodiments, the sdAb is modified position Leu 11 and Ala88. For example, L11E/A88E, L11E/A88D, L11E/A88K, L11E/A88R, L11D/A88E, L11D/A88D, L11D/A88K, L11D/A88R, L11K/A88E, L11K/A88D, L11K/A88K, L11K/A88R, L11R/A88E, L11R/A88D, L11R/A88K or L11R/A88R. In some embodiments, the sdAb is modified position Leu 11 and Ala88 and paired with a modified carboxy-terminal region. For example, L11E/A88E, L11E/A88D, L11E/A88K, L11E/A88R, L11D/A88E, L11D/A88D, L11D/A88K, L11D/A88R, L11K/A88E, L11K/A88D, L11K/A88K, L11K/A88R, L11R/A88E, L11R/A88D, L11R/A88K or L11R/A88R and comprising the terminal sequence of TVE, TVSE (SEQ ID NO: 24), TVEG (SEQ ID NO: 25), TVSEG (SEQ ID NO: 26), TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), TVRPGG (SEQ ID NO: 51), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), or TVDPGG (SEQ ID NO: 57).

BRIEF DESCRIPTION OF THE DRAWINGS

FIG. 4 is a graph of an ASDA assay demonstrating the impact of various modifications of an immunogenic sdAb in ASDA recognition. Enbrel (TNFR2-Fc) was included as non-ASDA recognized control. Herein framework 1 modifications were combined with framework 4 modifications.

DETAILED DESCRIPTION

Figure 1:
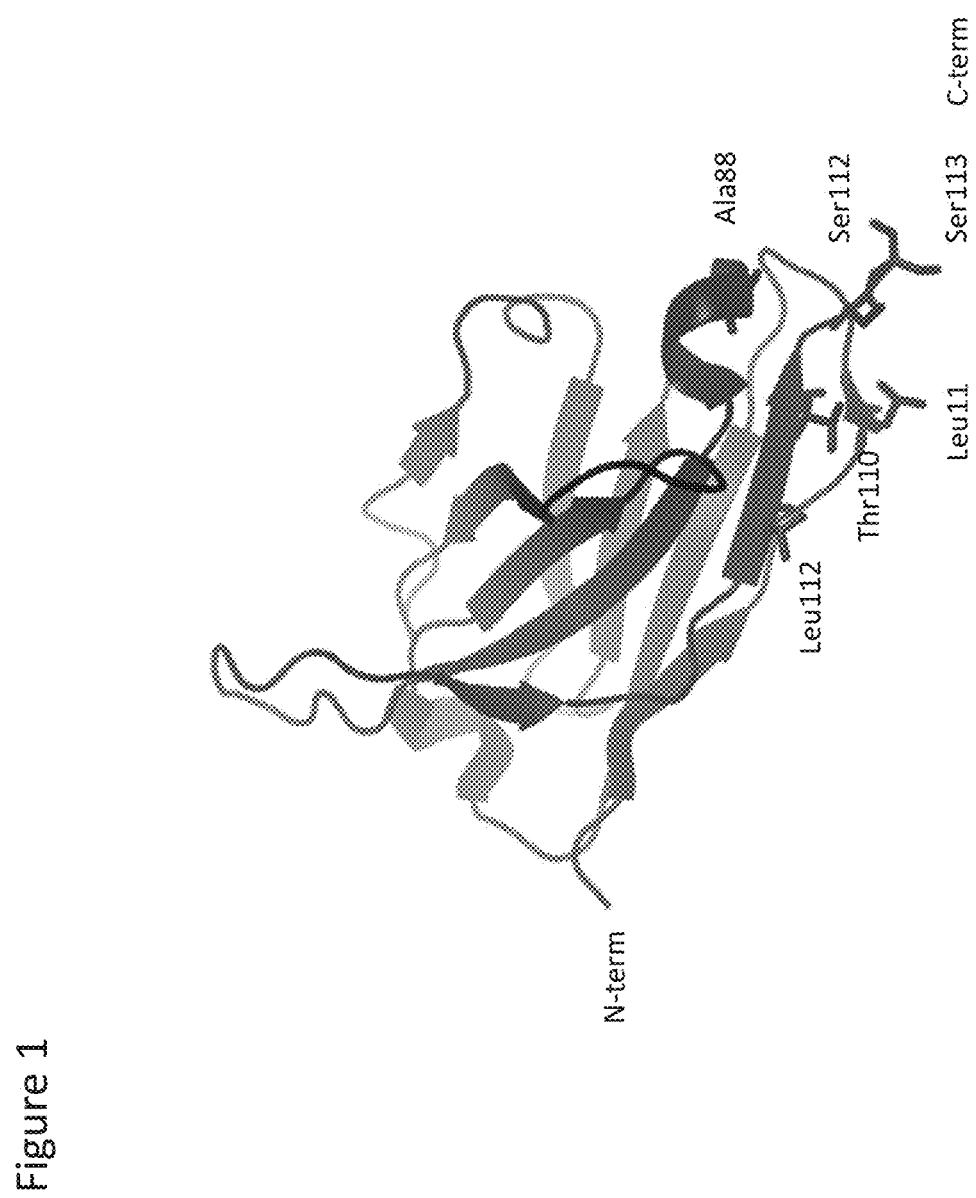
FIG. 1 is a schematic of structural model of VH domain highlighting exemplary positions that were modified to prevent ASDA recognition.

A single-domain antibody (sdAb) is an antibody fragment consisting of a single monomeric variable antibody domain that is able to bind selectively to a specific antigen. See e.g., Hamers-Casterman, C., et al., "Naturally occurring antibodies devoid of light chains," Nature vol. 363: 446-448 (1993); Nguyen, V. K., et al., "Camel heavy-chain antibodies: diverse germline V(H)H and specific mechanisms enlarge the antigen-binding repertoire," EMBO, vol. 19: 921-30 (2000); Achour, I., et al., "Tetrameric and homodimeric camelid IgGs originate from the same IgH locus," J. Immunol., vol. 181: 2001-2009 (2008); Harmsen, et al., "Llama heavy-chain V regions consist of at least four distinct subfamilies revealing novel sequence features," Mol. Immunol., vol. 37: 579-590 (2000); Arbabi Ghahroudi, M., et al., "Selection and identification of single domain antibody fragments from camel heavy-chain antibodies," FEBS Lett. vol. 414: 521-526 (1997); and Vincke et al., "General Strategy to Humanize a Camelid Single-domain Antibody and Identification of a Universal Humanized Nanobody Scaffold," J. Biol. Chem., vol. 284(5): 3273-84 (2009), the contents of each of which are hereby incorporated by reference in their entireties).

With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

A single-domain antibody can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen. (See e.g., Arbabi Ghahroudi, M.; Desmyter, A.; et al. (1997). "Selection and identification of single domain antibody fragments from camel heavy-chain antibodies". FEBS Letters 414 (3): 521-526.)

A different method uses gene libraries from animals that have not been immunized beforehand. Such naïve libraries usually contain only antibodies with low affinity to the desired antigen, making it necessary to apply affinity maturation by random mutagenesis as an additional step. (Saerens, D.; et al. (2008). "Single-domain antibodies as building blocks for novel therapeutics". Current Opinion in Pharmacology 8 (5): 600-608.)

When the most potent clones have been identified, their DNA sequence is optimized, for example to improve their stability towards enzymes. Another goal is humanization to prevent immunological reactions of the human organism against the antibody. Humanization is unproblematic because of the homology between camelid VHH and human VH fragments. (See e.g., Saerens, et al., (2008). "Single-domain antibodies as building blocks for novel therapeutics". Current Opinion in Pharmacology 8 (5): 600-608.) The final step is the translation of the optimized single-domain antibody in *E. coli, Saccharomyces cerevisiae* or other suitable organisms.

Single domain antibody fragments are also derived from conventional antibodies. In some embodiments, single-domain antibodies can be made from common murine or human IgG with four chains. (Holt, L. J.; et al. (2003). "Domain antibodies: proteins for therapy". Trends in Biotechnology 21 (11): 484-490.) The process is similar, comprising gene libraries from immunized or naïve donors and display techniques for identification of the most specific antigens. A problem with this approach is that the binding region of common IgG consists of two domains (VH and VL), which tend to dimerize or aggregate because of their lipophilicity. Monomerization is usually accomplished by replacing lipophilic by hydrophilic amino acids, but often results in a loss of affinity to the antigen. (See e.g., Borrebaeck, C. A. K.; Ohlin, M. (2002). "Antibody evolution beyond Nature". Nature Biotechnology 20 (12): 1189-90.) If affinity can be retained, the single-domain antibodies can likewise be produced in *E. coli, S. cerevisiae* or other organisms.

The modifications within human or humanized single domain antibody fragments described herein are useful with any single domain antibody fragment, regardless of method of production.

The invention provides a single domain antibody (sbAb) or antigen-binding fragments thereof that comprise at least one mutation that prevents recognition of the sbAb by an antibody that specifically recognizes single domain antibodies. In some embodiments, the mutation is at least one mutation in a framework region.

In some embodiments, the mutation is at least one framework 4 mutation. In some embodiments, the framework 4 mutation comprises an amino acid sequence selected from the group consisting of SEQ ID NO: 1-18 or 30-43.

In some embodiments, the mutation is a carboxy-terminal amino acid extension. In some embodiments, the carboxy-terminal amino acid extension comprises an amino acid sequence selected from the group consisting of SEQ ID NO: 19-23.

In some embodiments, the mutation is at least one framework 1 mutation. In some embodiments, the framework 1 mutation comprises a mutation at position Leu11. In some embodiments, the mutation at position Leu11 is Leu11Lys (L11K), Leu11Arg (L11R), Leu11Asp (L11D), or Leu11Glu (L11E). In some embodiments, the single domain antibody further comprises a mutation in the carboxy terminus. In some embodiments, the mutation in the carboxy terminus comprises an amino acid sequence selected from the group consisting of SEQ ID NO: 24-29 or 30-43. In some embodiments, the framework 1 region comprises Leu11Lys (L11K) and the mutation in the carboxy terminus comprises an amino acid sequence selected from the group consisting of TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57). In some embodiments, the framework 1 region comprises Leu11Glu (L11E) and the mutation in the carboxy terminus comprises an amino acid sequence selected from the group consisting of TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51).

In some embodiments, the mutation is at least one framework 3 mutation. In some embodiments, the framework 3 mutation comprises a mutation at position Ala88. In some embodiments, the mutation at position Ala88 is Ala88Glu (A88E), Ala88Asp (A88D), Ala88Arg (A88R), or Ala88Lys (A88K). In some embodiments, the single domain antibody further comprises a mutation in the carboxy terminus. In some embodiments, the mutation in the carboxy terminus comprises an amino acid sequence selected from the group consisting of SEQ ID NO: 24-29 and 44-57. In some embodiments, the framework 3 region comprises Ala88Glu (A88E) and the mutation in the carboxy terminus comprises an amino acid sequence selected from the group consisting of TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51). In some embodiments, the framework 3 region comprises Ala88Lys (A88K) and the mutation in the carboxy terminus comprises an amino acid sequence selected from the group consisting of TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

All patents and publications mentioned in this specification are herein incorporated by reference to the same extent as if each independent patent and publication was specifically and individually indicated to be incorporated by reference.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, Fab, Fab' and F(ab')$_2$ fragments, F$_v$, scFvs, an Fab expression library, and single domain antibody (sdAb) fragments, for example V$_H$H, V$_{NAR}$, engineered V$_H$ or V$_K$.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an antigen, when the equilibrium binding constant ($K_d$) is ≤1 µM, preferably ≤100 nM, more preferably ≤10 nM, and most preferably ≤100 pM to about 1 pM, as measured by assays such as radioligand binding assays, surface plasmon resonance (SPR), flow cytometry binding assay, or similar assays known to those skilled in the art.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation. (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Examples

A direct anti-single domain antibody (ASDA) detection assay is useful in determining pre-existing ASDA in serum from human donors. Generally, pre-existing antibodies within human serum can be identified by an ELISA wherein the sdAb is immobilized on a plate and blocked with BSA. Human serum (neat or diluted in PBS+0.01% Tween-20) is then incubated with the plate-bound sdAb. Unbound serum IgG is washed away and any remaining antibodies to the sdAb are detected using both anti-human IgKappa and anti-human IgLamda HRP-conjugated antibodies.

An indirect ASDA assay is useful for the analysis of multiple variants of a given sdAb so as to measure the sdAb specific serum antibody reactivity. The indirect ASDA involves immobilization of an sdAb and blocked with BSA. Human serum (neat or diluted in PBS+0.01% Tween-20) is then pre-incubated with soluble sdAb (either the same sdAb or variants of the parental sdAb with modifications of the present invention [mutations, truncation or extensions]), and then added to the plate bound sdAb. The ability of a soluble sdAb variant to block the ASDA recognition of the immobilized sdAb is indicative of the soluble sdAb being recognized by the ASDAs and is thus an indirect measurement of the pre-existing ASDA response. Conversely, the inability of a soluble sdAbs to prevent the ASDA recognition of the immobilized sdAb is indicative of the soluble sdAb variant being non-immunogenic or otherwise not recognized by the pre-existing ASDAs. Generally, 8-16 assays are conducted in parallel with serum from separate donors previously determined to contain ASDAs.

Figure 2:
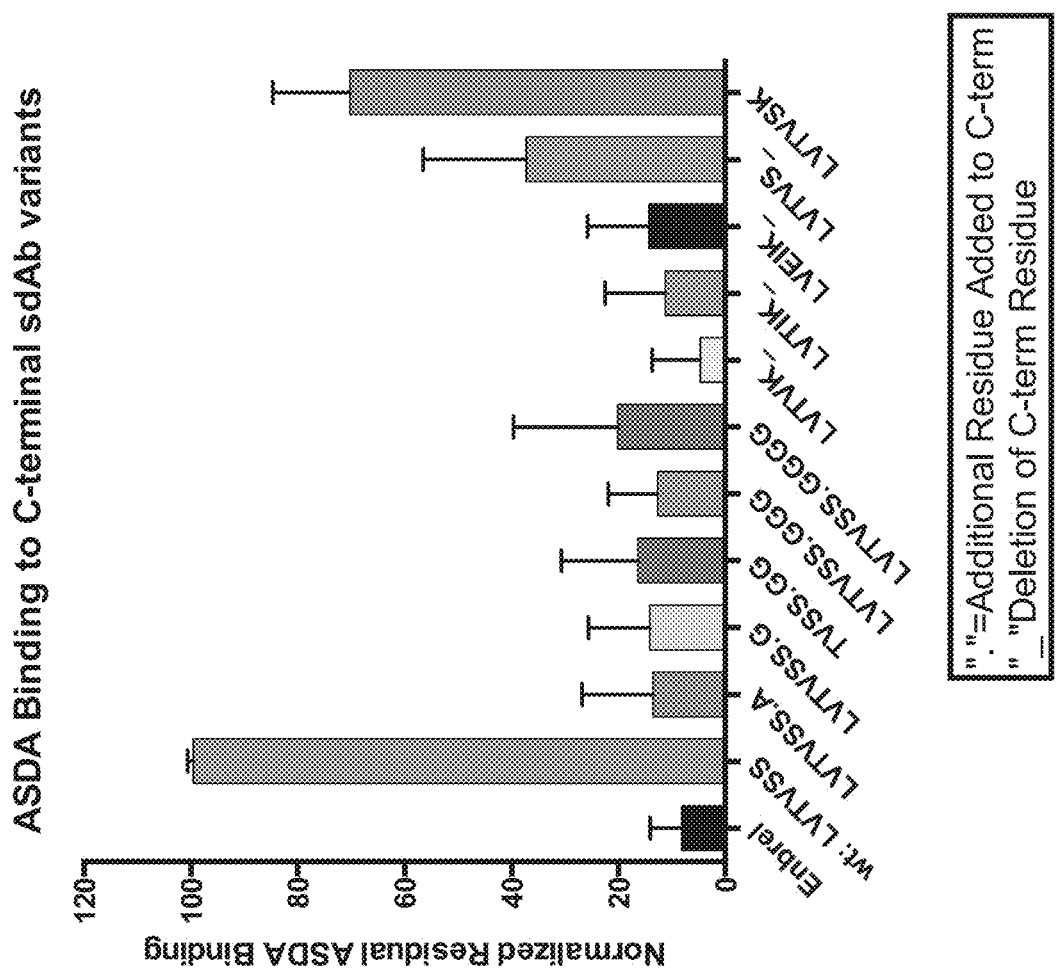
FIG. 2 is a graph of an ASDA assay demonstrating the impact of various exemplary modifications of an immunogenic sdAb in ASDA recognition. Enbrel (TNFR2-Fc) was included as non-ASDA recognized control. C-terminal extensions are indicated by a "." between the natural terminal residue and start of the extension. C-terminal truncations are indicated by a "_" at the site of excluded residue.
Figure 3A:
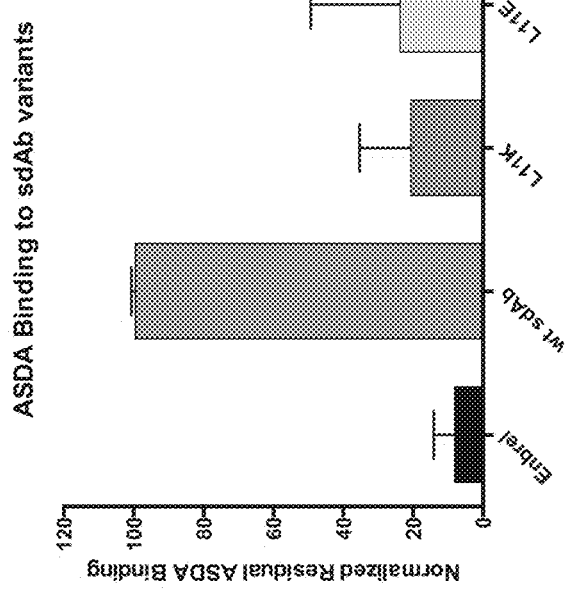
FIGS. 3A and 3B are a series of graphs of an ASDA assay demonstrating the impact of various modifications of an immunogenic sdAb in ASDA recognition. Enbrel (TNFR2-Fc) was included as non-ASDA recognized control.
Figure 3B:
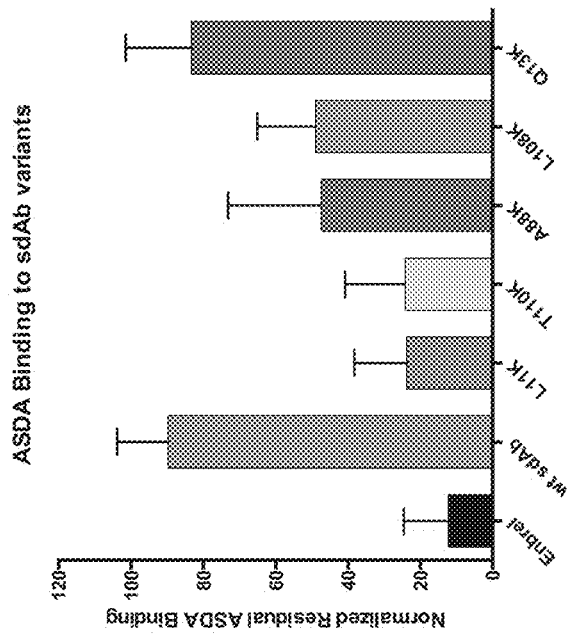
Figure 4:
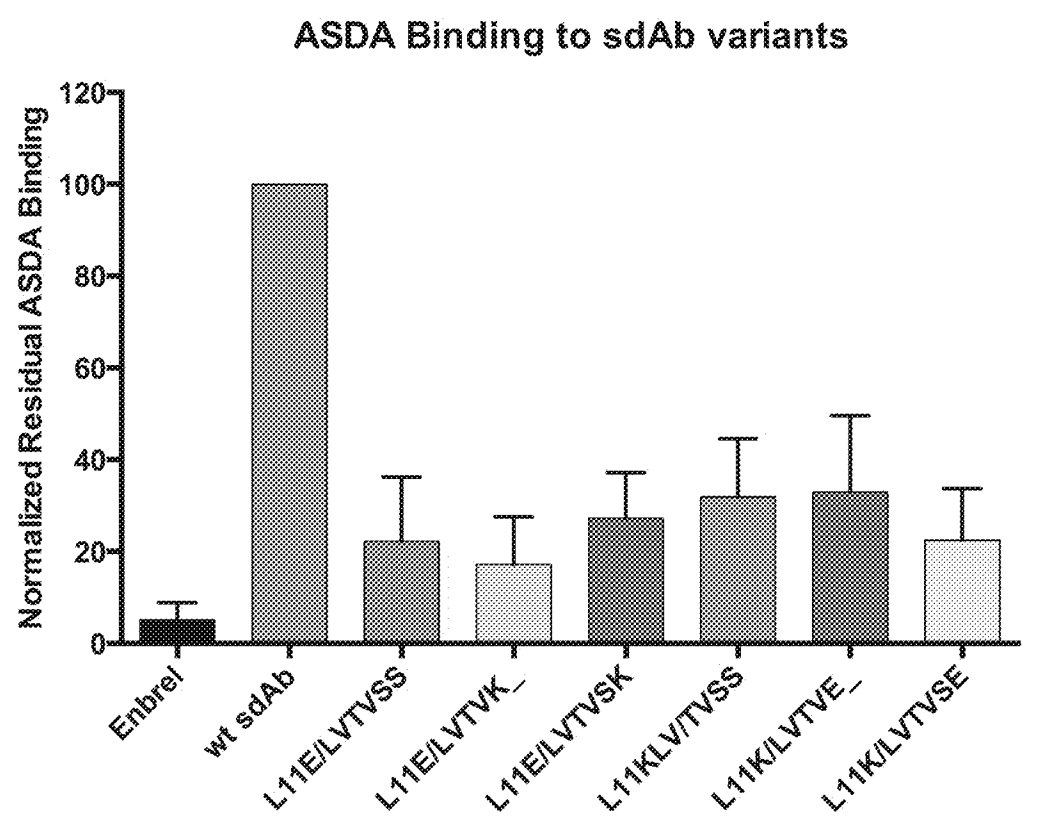

In the studies provided herein, various exemplary modifications of an immunogenic sdAb were evaluated using an ASDA assay. Enbrel (TNFR2-Fc) and BSA were sometimes included as non-ASDA recognized control. In some experiments purified serum IgG was coated as a positive control for the secondary antibodies. C-terminal extensions are indicated by a "." between the natural terminal residue and start of the extension. C-terminal truncations are indicated by a "_" at the site of excluded residue. The results are shown in FIGS. 2-4.

Figures 5A, 5B:
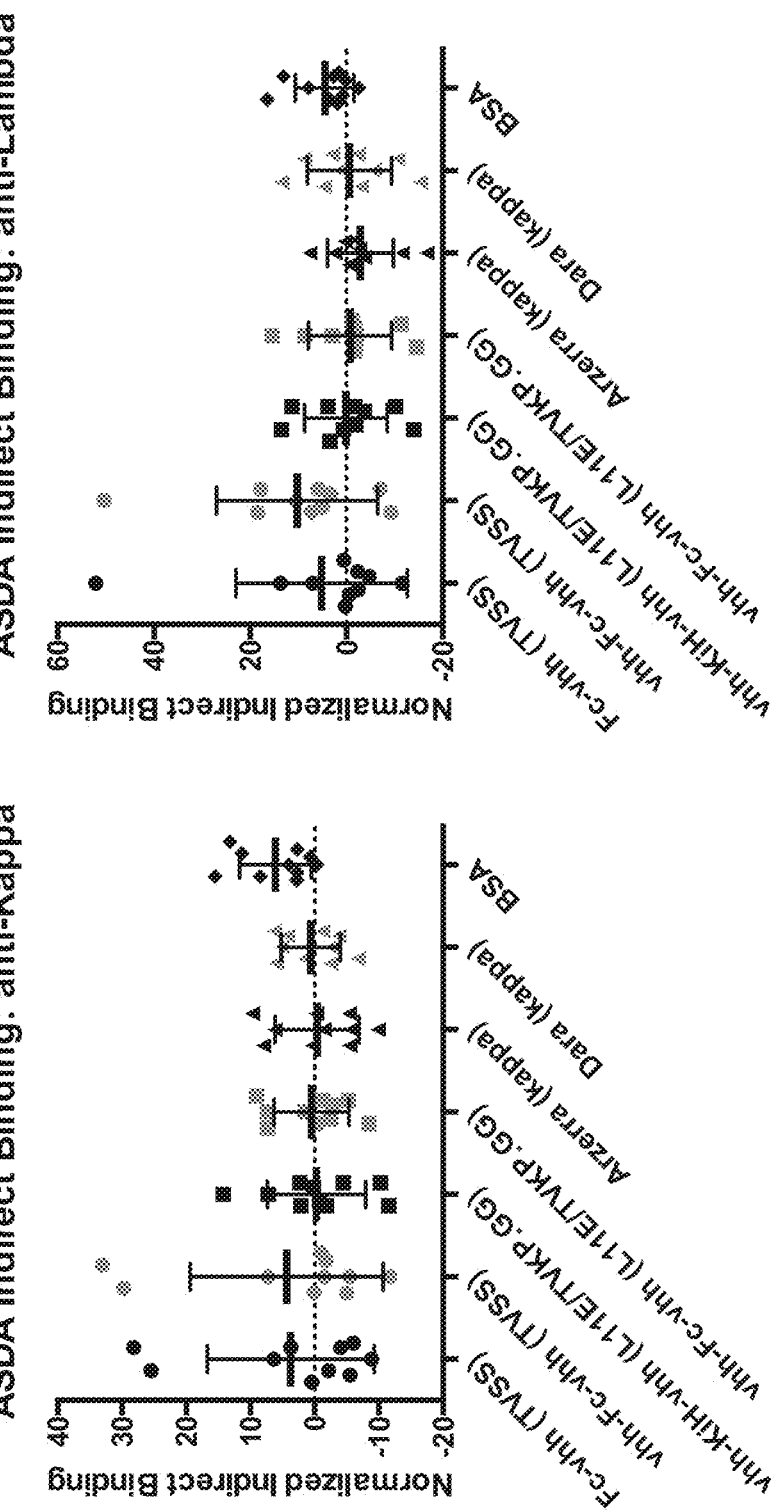
FIGS. 5A and 5B are a series of graphs of an indirect ASDA assay demonstrating the impact the dual modifications of a humanized VHH having of L11E paired with a carboxy-terminal TVKPGG compared with a humanized VHH unmodified at L11 and having the native carboxy-terminal sequence, TVSS.

An indirect ASDA assay demonstrated the impact the dual modifications of a humanized VHH having of L11E paired with a carboxy-terminal TVKPGG compared with a humanized VHH unmodified at L11 and having the native carboxy-terminal sequence, TVSS (FIGS. 5A-5B).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A single domain antibody (sdAb) comprising a mutation at position Leu11 according to Kabat, wherein the mutation at position Leu11 is Leu11Lys (L11K), Leu11Arg (L11R), Leu11Asp (L11D), or Leu11Glu (L11E), and wherein the carboxy terminus comprises an amino acid sequence selected from TVE, TVK, LVTVS (SEQ ID NO: 7), LVTVSS (SEQ ID NO: 113), TVSE (SEQ ID NO: 24), TVEG (SEQ ID NO: 25), TVSEG (SEQ ID NO: 26), TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), TVRPGG (SEQ ID NO: 51), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

2. The single domain antibody of claim 1, wherein the carboxy terminus comprises an amino acid sequence selected from SEQ ID NOs: 2-10 and 30-43.

3. The single domain antibody of claim 1, wherein the mutation at position Leu11 is Leu11Lys (L11K) and the carboxy terminus comprises an amino acid sequence selected from TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

4. The single domain antibody of claim 1, wherein the mutation at position Leu11 is Leu11Glu (L11E) and the carboxy terminus comprises an amino acid sequence selected from TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51).

5. The single domain antibody of claim 1, wherein the mutation at position Leu11 is Leu11Glu (L11E) and the carboxy terminus comprises an amino acid sequence selected from TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

6. The single domain antibody of claim 1, wherein the mutation at position Leu11 is Leu11Lys (L11K) and the carboxy terminus comprises an amino acid sequence selected from TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51).

7. The single domain antibody of claim 1, wherein the mutation at position Leu11 is Leu11Glu (L11E) and the carboxy terminus of the single domain antibody comprises the amino acid sequence of SEQ ID NO: 48 or SEQ ID NO: 34.

8. The single domain antibody of claim 1, wherein the mutation at position Leu11 is Leu11Glu (L11E) and the carboxy terminus of the single domain antibody comprises the amino acid sequence of SEQ ID NO: 47 or SEQ ID NO: 33.

9. The single domain antibody of claim 1, wherein the mutation at position Leu11 is Leu11Arg (L11R) and the carboxy terminus comprises an amino acid sequence selected from TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

10. The single domain antibody of claim 1, wherein the mutation at position Leu11 is Leu11Arg (L11R) and the carboxy terminus comprises an amino acid sequence selected from TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51).

11. The single domain antibody of claim 1, wherein the mutation at position Leu11 is Leu11Asp (L11D) and the carboxy terminus comprises an amino acid sequence selected from TVE, TVSE (SEQ ID NO: 24), TVEG (SEQ ID NO: 25), TVSEG (SEQ ID NO: 26), TVEP (SEQ ID NO: 52), TVEPG (SEQ ID NO: 53), TVEPGG (SEQ ID NO: 54), TVDP (SEQ ID NO: 55), TVDPG (SEQ ID NO: 56), and TVDPGG (SEQ ID NO: 57).

12. The single domain antibody of claim 1, wherein the mutation at position Leu11 is Leu11Asp (L11D) and the carboxy terminus comprises an amino acid sequence selected from TVK, TVSK (SEQ ID NO: 27), TVKG (SEQ ID NO: 28), TVSKG (SEQ ID NO: 29), TVSKPG (SEQ ID NO: 44), TVSKPGG (SEQ ID NO: 45), TVKP (SEQ ID NO: 46), TVKPG (SEQ ID NO: 47), TVKPGG (SEQ ID NO: 48), TVRP (SEQ ID NO: 49), TVRPG (SEQ ID NO: 50), and TVRPGG (SEQ ID NO: 51).

13. The single domain antibody of claim 1, wherein the mutation at position Leu11 is Leu11Glu (L11E) and the carboxy terminus of the single domain antibody comprises the amino acid sequence TVKP (SEQ ID NO: 46).

14. The single domain antibody of claim 1, wherein the mutation at position Leu11 is Leu11Glu (L11E) and the carboxy terminus of the single domain antibody comprises the amino acid sequence TVK.

15. The single domain antibody of claim 1, wherein the mutation at position Leu11 is Leu11Glu (L11E) and the carboxy terminus of the single domain antibody comprises the amino acid sequence TVRP (SEQ ID NO: 49), TVRPG (SEQ ID NO: 50), or TVRPGG (SEQ ID NO: 51).

16. The single domain antibody of claim 1, wherein the mutation at position Leu11 is Leu11Asp (L11D) and the carboxy terminus of the single domain antibody comprises the amino acid sequence of TVKPGG (SEQ ID NO: 48).

17. The single domain antibody of claim 1, wherein the mutation at position Leu11 is Leu11Asp (L11D) and the carboxy terminus of the single domain antibody comprises the amino acid sequence of TVKPG (SEQ ID NO: 47).

18. The single domain antibody of claim 1, wherein the mutation at position Leu11 is Leu11Asp (L11D) and the carboxy terminus of the single domain antibody comprises the amino acid sequence TVKP (SEQ ID NO: 46).

19. The single domain antibody of claim 1, wherein the mutation at position Leu11 is Leu11Asp (L11D) and the carboxy terminus of the single domain antibody comprises the amino acid sequence TVK.

20. The single domain antibody of claim 1, wherein the mutation at position Leu11 is Leu11Asp (L11D) and the carboxy terminus of the single domain antibody comprises the amino acid sequence TVRP (SEQ ID NO: 49), TVRPG (SEQ ID NO: 50), or TVRPGG (SEQ ID NO: 51).

21. The single domain antibody of claim 1, wherein the mutation at position Leu11 is Leu11Lys (L11K) and the carboxy terminus of the single domain antibody comprises the amino acid sequence TVE, TVEP (SEQ ID NO: 52), TVEPG (SEQ ID NO: 53), or TVEPGG (SEQ ID NO: 54).

22. The single domain antibody of claim 1, wherein the mutation at position Leu11 is Leu11Lys (L11K) and the carboxy terminus of the single domain antibody comprises the amino acid sequence TVDP (SEQ ID NO: 55), TVDPG (SEQ ID NO: 56), or TVDPGG (SEQ ID NO: 57).

23. The single domain antibody of claim 1, wherein the mutation at position Leu11 is Leu11Arg (L11R) and the carboxy terminus of the single domain antibody comprises the amino acid sequence TVE, TVEP (SEQ ID NO: 52), TVEPG (SEQ ID NO: 53), or TVEPGG (SEQ ID NO: 54).

24. The single domain antibody of claim 1, wherein the mutation at position Leu11 is Leu11Arg (L11R) and the carboxy terminus of the single domain antibody comprises the amino acid sequence TVDP (SEQ ID NO: 55), TVDPG (SEQ ID NO: 56), or TVDPGG (SEQ ID NO: 57).

* * * * *

UNITED STATES PATENT AND TRADEMARK OFFICE
CERTIFICATE OF CORRECTION

PATENT NO. : 10,526,397 B2
APPLICATION NO. : 15/003234
DATED : January 7, 2020
INVENTOR(S) : Brendan P. Eckelman, John C. Timmer and Quinn Deveraux Page 1 of 1

It is certified that error appears in the above-identified patent and that said Letters Patent is hereby corrected as shown below:

In the Claims

In Claim 1, at Column 31, Line 57, the text "LVTVSS (SEQ ID: 113)" is replaced with --LVTVSS (SEQ ID: 58)--.

Signed and Sealed this
Fifth Day of May, 2020

Andrei Iancu
*Director of the United States Patent and Trademark Office*

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: chemically synthesized

<400> SEQUENCE: 1

Leu Val Glu Ile Lys
1               5

<210> SEQ ID NO 2
<211> LENGTH: 5
<212> TYPE: PRT
<213> ORGANISM: Artificial Sequence
<220> FEATURE:
<223> OTHER INFORMATION: chemically synthesized

<400> SEQUENCE: 2

Leu Val Thr Val Glu
1               5

<210> SEQ ID NO 3
<211> LENGTH: 6
<212> TYPE: PRT
<213> ORGANISM: Artificial Sequence
<220> FEATURE:
<223> OTHER INFORMATION: chemically synthesized

<400> SEQUENCE: 3

Leu Val Thr Val Ser Glu
1               5

<210> SEQ ID NO 4
<211> LENGTH: 6
<212> TYPE: PRT
<213> ORGANISM: Artificial Sequence
<220> FEATURE:
<223> OTHER INFORMATION: chemically synthesized

<400> SEQUENCE: 4

Leu Val Thr Val Glu Gly
1               5

<210> SEQ ID NO 5
<211> LENGTH: 7
<212> TYPE: PRT
<213> ORGANISM: Artificial Sequence
<220> FEATURE:
<223> OTHER INFORMATION: chemically synthesized

<400> SEQUENCE: 5

Leu Val Thr Val Ser Glu Gly
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: chemically synthesized

<400> SEQUENCE: 6

Leu Val Thr Val Lys
1               5

<210> SEQ ID NO 7
<211> LENGTH: 5
<212> TYPE: PRT
<213> ORGANISM: Artificial Sequence
<220> FEATURE:
<223> OTHER INFORMATION: chemically synthesized

<400> SEQUENCE: 7

Leu Val Thr Val Ser
1               5

<210> SEQ ID NO 8
<211> LENGTH: 6
<212> TYPE: PRT
<213> ORGANISM: Artificial Sequence
<220> FEATURE:
<223> OTHER INFORMATION: chemically synthesized

<400> SEQUENCE: 8

Leu Val Thr Val Ser Lys
1               5

<210> SEQ ID NO 9
<211> LENGTH: 6
<212> TYPE: PRT
<213> ORGANISM: Artificial Sequence
<220> FEATURE:
<223> OTHER INFORMATION: chemically synthesized

<400> SEQUENCE: 9

Leu Val Thr Val Lys Gly
1               5

<210> SEQ ID NO 10
<211> LENGTH: 7
<212> TYPE: PRT
<213> ORGANISM: Artificial Sequence
<220> FEATURE:
<223> OTHER INFORMATION: chemically synthesized

<400> SEQUENCE: 10

Leu Val Thr Val Ser Lys Gly
1               5

<210> SEQ ID NO 11
<211> LENGTH: 6
<212> TYPE: PRT
<213> ORGANISM: Artificial Sequence
<220> FEATURE:
<223> OTHER INFORMATION: chemically synthesized

<400> SEQUENCE: 11

Glu Val Thr Val Ser Ser
1               5

<210> SEQ ID NO 12
```

```
<211> LENGTH: 6
<212> TYPE: PRT
<213> ORGANISM: Artificial Sequence
<220> FEATURE:
<223> OTHER INFORMATION: chemically synthesized

<400> SEQUENCE: 12

Lys Val Thr Val Ser Ser
1               5

<210> SEQ ID NO 13
<211> LENGTH: 6
<212> TYPE: PRT
<213> ORGANISM: Artificial Sequence
<220> FEATURE:
<223> OTHER INFORMATION: chemically synthesized

<400> SEQUENCE: 13

Leu Val Glu Val Ser Ser
1               5

<210> SEQ ID NO 14
<211> LENGTH: 6
<212> TYPE: PRT
<213> ORGANISM: Artificial Sequence
<220> FEATURE:
<223> OTHER INFORMATION: chemically synthesized

<400> SEQUENCE: 14

Leu Val Lys Val Ser Ser
1               5

<210> SEQ ID NO 15
<211> LENGTH: 6
<212> TYPE: PRT
<213> ORGANISM: Artificial Sequence
<220> FEATURE:
<223> OTHER INFORMATION: chemically synthesized

<400> SEQUENCE: 15

Glu Val Glu Val Ser Ser
1               5

<210> SEQ ID NO 16
<211> LENGTH: 6
<212> TYPE: PRT
<213> ORGANISM: Artificial Sequence
<220> FEATURE:
<223> OTHER INFORMATION: chemically synthesized

<400> SEQUENCE: 16

Glu Val Lys Val Ser Ser
1               5

<210> SEQ ID NO 17
<211> LENGTH: 6
<212> TYPE: PRT
<213> ORGANISM: Artificial Sequence
<220> FEATURE:
<223> OTHER INFORMATION: chemically synthesized

<400> SEQUENCE: 17

Lys Val Lys Val Ser Ser
1               5

<210> SEQ ID NO 18
<211> LENGTH: 6
```

```
<212> TYPE: PRT
<213> ORGANISM: Artificial Sequence
<220> FEATURE:
<223> OTHER INFORMATION: chemically synthesized

<400> SEQUENCE: 18

Lys Val Glu Val Ser Ser
1               5

<210> SEQ ID NO 19
<211> LENGTH: 7
<212> TYPE: PRT
<213> ORGANISM: Artificial Sequence
<220> FEATURE:
<223> OTHER INFORMATION: chemically synthesized

<400> SEQUENCE: 19

Leu Val Thr Val Ser Ser Ala
1               5

<210> SEQ ID NO 20
<211> LENGTH: 7
<212> TYPE: PRT
<213> ORGANISM: Artificial Sequence
<220> FEATURE:
<223> OTHER INFORMATION: chemically synthesized

<400> SEQUENCE: 20

Leu Val Thr Val Ser Ser Gly
1               5

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Leu Val Thr Val Ser Ser Gly Gly
1               5

<210> SEQ ID NO 22
<211> LENGTH: 9
<212> TYPE: PRT
<213> ORGANISM: Artificial Sequence
<220> FEATURE:
<223> OTHER INFORMATION: chemically synthesized

<400> SEQUENCE: 22

Leu Val Thr Val Ser Ser Gly Gly Gly
1               5

<210> SEQ ID NO 23
<211> LENGTH: 10
<212> TYPE: PRT
<213> ORGANISM: Artificial Sequence
<220> FEATURE:
<223> OTHER INFORMATION: chemically synthesized

<400> SEQUENCE: 23

Leu Val Thr Val Ser Ser Gly Gly Gly Gly
1               5                   10

<210> SEQ ID NO 24
<211> LENGTH: 4
<212> TYPE: PRT
```

```
<213> ORGANISM: Artificial Sequence
<220> FEATURE:
<223> OTHER INFORMATION: chemically synthesized

<400> SEQUENCE: 24

Thr Val Ser Glu
1

<210> SEQ ID NO 25
<211> LENGTH: 4
<212> TYPE: PRT
<213> ORGANISM: Artificial Sequence
<220> FEATURE:
<223> OTHER INFORMATION: chemically synthesized

<400> SEQUENCE: 25

Thr Val Glu Gly
1

<210> SEQ ID NO 26
<211> LENGTH: 5
<212> TYPE: PRT
<213> ORGANISM: Artificial Sequence
<220> FEATURE:
<223> OTHER INFORMATION: chemically synthesized

<400> SEQUENCE: 26

Thr Val Ser Glu Gly
1               5

<210> SEQ ID NO 27
<211> LENGTH: 4
<212> TYPE: PRT
<213> ORGANISM: Artificial Sequence
<220> FEATURE:
<223> OTHER INFORMATION: chemically synthesized

<400> SEQUENCE: 27

Thr Val Ser Lys
1

<210> SEQ ID NO 28
<211> LENGTH: 4
<212> TYPE: PRT
<213> ORGANISM: Artificial Sequence
<220> FEATURE:
<223> OTHER INFORMATION: chemically synthesized

<400> SEQUENCE: 28

Thr Val Lys Gly
1

<210> SEQ ID NO 29
<211> LENGTH: 5
<212> TYPE: PRT
<213> ORGANISM: Artificial Sequence
<220> FEATURE:
<223> OTHER INFORMATION: chemically synthesized

<400> SEQUENCE: 29

Thr Val Ser Lys Gly
1               5

<210> SEQ ID NO 30
<211> LENGTH: 8
<212> TYPE: PRT
<213> ORGANISM: Artificial Sequence
```

```
<220> FEATURE:
<223> OTHER INFORMATION: chemically synthesized

<400> SEQUENCE: 30

Leu Val Thr Val Ser Lys Pro Gly
1               5

<210> SEQ ID NO 31
<211> LENGTH: 9
<212> TYPE: PRT
<213> ORGANISM: Artificial Sequence
<220> FEATURE:
<223> OTHER INFORMATION: chemically synthesized

<400> SEQUENCE: 31

Leu Val Thr Val Ser Lys Pro Gly Gly
1               5

<210> SEQ ID NO 32
<211> LENGTH: 6
<212> TYPE: PRT
<213> ORGANISM: Artificial Sequence
<220> FEATURE:
<223> OTHER INFORMATION: chemically synthesized

<400> SEQUENCE: 32

Leu Val Thr Val Lys Pro
1               5

<210> SEQ ID NO 33
<211> LENGTH: 7
<212> TYPE: PRT
<213> ORGANISM: Artificial Sequence
<220> FEATURE:
<223> OTHER INFORMATION: chemically synthesized

<400> SEQUENCE: 33

Leu Val Thr Val Lys Pro Gly
1               5

<210> SEQ ID NO 34
<211> LENGTH: 8
<212> TYPE: PRT
<213> ORGANISM: Artificial Sequence
<220> FEATURE:
<223> OTHER INFORMATION: chemically synthesized

<400> SEQUENCE: 34

Leu Val Thr Val Lys Pro Gly Gly
1               5

<210> SEQ ID NO 35
<211> LENGTH: 6
<212> TYPE: PRT
<213> ORGANISM: Artificial Sequence
<220> FEATURE:
<223> OTHER INFORMATION: chemically synthesized

<400> SEQUENCE: 35

Leu Val Thr Val Arg Pro
1               5

<210> SEQ ID NO 36
<211> LENGTH: 7
<212> TYPE: PRT
<213> ORGANISM: Artificial Sequence
<220> FEATURE:
```

<223> OTHER INFORMATION: chemically synthesized

<400> SEQUENCE: 36

Leu Val Thr Val Arg Pro Gly
1               5

<210> SEQ ID NO 37
<211> LENGTH: 8
<212> TYPE: PRT
<213> ORGANISM: Artificial Sequence
<220> FEATURE:
<223> OTHER INFORMATION: chemically synthesized

<400> SEQUENCE: 37

Leu Val Thr Val Arg Pro Gly Gly
1               5

<210> SEQ ID NO 38
<211> LENGTH: 6
<212> TYPE: PRT
<213> ORGANISM: Artificial Sequence
<220> FEATURE:
<223> OTHER INFORMATION: chemically synthesized

<400> SEQUENCE: 38

Leu Val Thr Val Glu Pro
1               5

<210> SEQ ID NO 39
<211> LENGTH: 7
<212> TYPE: PRT
<213> ORGANISM: Artificial Sequence
<220> FEATURE:
<223> OTHER INFORMATION: chemically synthesized

<400> SEQUENCE: 39

Leu Val Thr Val Glu Pro Gly
1               5

<210> SEQ ID NO 40
<211> LENGTH: 8
<212> TYPE: PRT
<213> ORGANISM: Artificial Sequence
<220> FEATURE:
<223> OTHER INFORMATION: chemically synthesized

<400> SEQUENCE: 40

Leu Val Thr Val Glu Pro Gly Gly
1               5

<210> SEQ ID NO 41
<211> LENGTH: 6
<212> TYPE: PRT
<213> ORGANISM: Artificial Sequence
<220> FEATURE:
<223> OTHER INFORMATION: chemically synthesized

<400> SEQUENCE: 41

Leu Val Thr Val Asp Pro
1               5

<210> SEQ ID NO 42
<211> LENGTH: 7
<212> TYPE: PRT
<213> ORGANISM: Artificial Sequence
<220> FEATURE:
<223> OTHER INFORMATION: chemically synthesized

```
<400> SEQUENCE: 42

Leu Val Thr Val Asp Pro Gly
1               5

<210> SEQ ID NO 43
<211> LENGTH: 8
<212> TYPE: PRT
<213> ORGANISM: Artificial Sequence
<220> FEATURE:
<223> OTHER INFORMATION: chemically synthesized

<400> SEQUENCE: 43

Leu Val Thr Val Asp Pro Gly Gly
1               5

<210> SEQ ID NO 44
<211> LENGTH: 6
<212> TYPE: PRT
<213> ORGANISM: Artificial Sequence
<220> FEATURE:
<223> OTHER INFORMATION: chemically synthesized

<400> SEQUENCE: 44

Thr Val Ser Lys Pro Gly
1               5

<210> SEQ ID NO 45
<211> LENGTH: 7
<212> TYPE: PRT
<213> ORGANISM: Artificial Sequence
<220> FEATURE:
<223> OTHER INFORMATION: chemically synthesized

<400> SEQUENCE: 45

Thr Val Ser Lys Pro Gly Gly
1               5

<210> SEQ ID NO 46
<211> LENGTH: 4
<212> TYPE: PRT
<213> ORGANISM: Artificial Sequence
<220> FEATURE:
<223> OTHER INFORMATION: chemically synthesized

<400> SEQUENCE: 46

Thr Val Lys Pro
1

<210> SEQ ID NO 47
<211> LENGTH: 5
<212> TYPE: PRT
<213> ORGANISM: Artificial Sequence
<220> FEATURE:
<223> OTHER INFORMATION: chemically synthesized

<400> SEQUENCE: 47

Thr Val Lys Pro Gly
1               5

<210> SEQ ID NO 48
<211> LENGTH: 6
<212> TYPE: PRT
<213> ORGANISM: Artificial Sequence
<220> FEATURE:
<223> OTHER INFORMATION: chemically synthesized
```

```
<400> SEQUENCE: 48

Thr Val Lys Pro Gly Gly
1               5

<210> SEQ ID NO 49
<211> LENGTH: 4
<212> TYPE: PRT
<213> ORGANISM: Artificial Sequence
<220> FEATURE:
<223> OTHER INFORMATION: chemically synthesized

<400> SEQUENCE: 49

Thr Val Arg Pro
1

<210> SEQ ID NO 50
<211> LENGTH: 5
<212> TYPE: PRT
<213> ORGANISM: Artificial Sequence
<220> FEATURE:
<223> OTHER INFORMATION: chemically synthesized

<400> SEQUENCE: 50

Thr Val Arg Pro Gly
1               5

<210> SEQ ID NO 51
<211> LENGTH: 6
<212> TYPE: PRT
<213> ORGANISM: Artificial Sequence
<220> FEATURE:
<223> OTHER INFORMATION: chemically synthesized

<400> SEQUENCE: 51

Thr Val Arg Pro Gly Gly
1               5

<210> SEQ ID NO 52
<211> LENGTH: 4
<212> TYPE: PRT
<213> ORGANISM: Artificial Sequence
<220> FEATURE:
<223> OTHER INFORMATION: chemically synthesized

<400> SEQUENCE: 52

Thr Val Glu Pro
1

<210> SEQ ID NO 53
<211> LENGTH: 5
<212> TYPE: PRT
<213> ORGANISM: Artificial Sequence
<220> FEATURE:
<223> OTHER INFORMATION: chemically synthesized

<400> SEQUENCE: 53

Thr Val Glu Pro Gly
1               5

<210> SEQ ID NO 54
<211> LENGTH: 6
<212> TYPE: PRT
<213> ORGANISM: Artificial Sequence
<220> FEATURE:
<223> OTHER INFORMATION: chemically synthesized

<400> SEQUENCE: 54
```

```
Thr Val Glu Pro Gly Gly
1               5

<210> SEQ ID NO 55
<211> LENGTH: 4
<212> TYPE: PRT
<213> ORGANISM: Artificial Sequence
<220> FEATURE:
<223> OTHER INFORMATION: chemically synthesized

<400> SEQUENCE: 55

Thr Val Asp Pro
1

<210> SEQ ID NO 56
<211> LENGTH: 5
<212> TYPE: PRT
<213> ORGANISM: Artificial Sequence
<220> FEATURE:
<223> OTHER INFORMATION: chemically synthesized

<400> SEQUENCE: 56

Thr Val Asp Pro Gly
1               5

<210> SEQ ID NO 57
<211> LENGTH: 6
<212> TYPE: PRT
<213> ORGANISM: Artificial Sequence
<220> FEATURE:
<223> OTHER INFORMATION: chemically synthesized

<400> SEQUENCE: 57

Thr Val Asp Pro Gly Gly
1               5

<210> SEQ ID NO 58
<211> LENGTH: 6
<212> TYPE: PRT
<213> ORGANISM: Artificial Sequence
<220> FEATURE:
<223> OTHER INFORMATION: chemically synthesized

<400> SEQUENCE: 58

Leu Val Thr Val Ser Ser
1               5
```